US008763816B2

(12) United States Patent
Andou et al.

(10) Patent No.: US 8,763,816 B2
(45) Date of Patent: Jul. 1, 2014

(54) FILTER FOR PROCESSING BLOOD

(75) Inventors: Michiyo Andou, Tokyo (JP); Tomohisa Yokomizo, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 481 days.

(21) Appl. No.: 13/074,093

(22) Filed: Mar. 29, 2011

(65) Prior Publication Data
US 2011/0240549 A1    Oct. 6, 2011

Related U.S. Application Data

(60) Provisional application No. 61/318,878, filed on Mar. 30, 2010.

(51) Int. Cl.
*B01D 29/88* (2006.01)
*B01D 29/00* (2006.01)

(52) U.S. Cl.
USPC ............ 210/435; 210/645; 210/782; 210/445

(58) Field of Classification Search
USPC ................................. 210/435, 645, 782, 445
See application file for complete search history.

(56) References Cited

U.S. PATENT DOCUMENTS

| | | | |
|---|---|---|---|
| 5,798,041 A | 8/1998 | Zur, Jr. | |
| 6,010,633 A | 1/2000 | Zur, Jr. et al. | |
| 6,030,539 A * | 2/2000 | Zuk, Jr. | 210/767 |
| 6,168,718 B1 | 1/2001 | Sutter et al. | |
| 6,601,710 B2 * | 8/2003 | Calhoun et al. | 210/435 |
| 2001/0037978 A1 | 11/2001 | Calhoun et al. | |
| 2002/0063090 A1 | 5/2002 | Calhoun et al. | |

FOREIGN PATENT DOCUMENTS

| | | |
|---|---|---|
| JP | 4-329965 | 11/1992 |
| JP | 11-513298 | 11/1999 |
| JP | 2001-503656 | 3/2001 |
| JP | 2001-508702 | 7/2001 |
| JP | 2002-541941 | 12/2002 |
| WO | 95/07818 | 3/1995 |
| WO | 00/62891 | 10/2000 |
| WO | 2008/103142 | 8/2008 |

OTHER PUBLICATIONS

Search report from International Bureau of WIPO, mail date is Jun. 21, 2011.

* cited by examiner

*Primary Examiner* — Nam Nguyen
*Assistant Examiner* — Madeline Gonzalez
(74) *Attorney, Agent, or Firm* — Greenblum & Bernstein P.L.C.

(57) ABSTRACT

A filter for processing blood that comprises a flexible container having an inlet and an outlet for blood, and a sheet-like blood processing filter material situated in such a manner so as to partition the inside of the container into an inlet side and an outlet side, wherein the flexible container comprises a container body which houses the blood processing filter material and an outlet port that forms the outlet, and the outlet port has a protrusion that protrudes from the container body into the inside of the container body, the protrusion having a plurality of fluid channel inlets formed at locations that are not in contact with the blood processing filter material.

11 Claims, 12 Drawing Sheets

FILTER FOR PROCESSING BLOOD

RELATED APPLICATION

This application is a non-provisional application based on Provisional Application Ser. No. 61/318,878 filed Mar. 30, 2010, and entitled FILTER FOR TREATING BLOOD.

BACKGROUND OF TUE INVENTION

1. Field of the Invention

The present invention relates to a filter for processing blood, which serves to remove undesirable components such as aggregates and leukocytes from blood. In particular, it relates to a precise and disposable filter for processing blood, to be used for removal of side-effect-causing microaggregates and leukocytes from blood transfusion-intended whole blood preparations, erythrocyte preparations, platelet preparations, blood plasma preparations and the like, and more particularly to a flexible filter wherein a resin material or the like is used as the container material.

2. Related Background of the Invention

Separation of whole blood collected from donors into blood components, such as erythrocyte preparations, platelet preparations and blood plasma preparations, and blood transfusion following their storage, is becoming a common procedure. Because the microaggregates and leukocytes present in such blood preparations are a cause of numerous blood transfusion side-effects, many methods are carried out by blood transfusion after removal of the undesirable components prior to the blood transfusion, or the use of blood transfusions from which the undesirable components have been removed following blood collection and storage.

The most common method for removing leukocytes from blood preparations involves treatment of the blood preparation using a leukocyte removal filter. Leukocyte removal filters include two types, leukocyte removal filters with flexible containers, employing as the container a material that is flexible and has excellent vapor permeability, identical or similar to one employing a filter element made of a nonwoven fabric or porous body in the bag of a blood collection separation set, and those having a filter element comprising a nonwoven fabric or porous body packed into a hard container of polycarbonate or the like.

For common treatment of blood with such leukocyte removal filters, a bag containing the blood preparation to be treated, which is connected to the blood inlet side of the filter via a blood tube, is placed at a position about 20 cm to 100 cm higher than the filter, the blood preparation passes through the filter by the action of gravity, and the filtered blood preparation is received in a collection bag connected to the blood outlet side of the filter via a blood tube. In the case of a leukocyte removal filter with a flexible container, pressure loss occurs due to the resistance of the filter element during filtering, causing the space on the filter inlet side to be at positive pressure. With a filter comprising a flexible container, the flexibility of the container causes the container to warp into a balloon shape under the positive pressure, such that the filter element presses against the container on the outlet side.

In the gap between the outlet container and filter element, on the other hand, since blood in the blood tube connected to the outlet falls by gravity and attempts to move into the bag provided for collection of the filtered blood, which is normally placed at a location 50-100 cm lower than the filter, this action produces negative pressure and the flexible container thus tends to stick to the filter element. That is, the filter element sticks to the container on the outlet side by double force, and flow of the blood is inhibited.

Relatively inexpensive hard containers such as polycarbonate, that can withstand autoclave sterilization, may be employed to prevent sticking of the filter element to the container at the outlet side. However, considering that sterilization of the entire apparatus is necessary if it is to be used for treatment of a blood preparation, packing into a hard container impairs the vapor permeability and necessitates a prolonged sterilization time. Moreover, prolonged autoclave sterilization leads to deterioration of preserved blood, and therefore filter sterilization must be followed by complicated procedures such as sterilization after connecting the blood bag, circuits and the like.

SUMMARY OF THE INVENTION

It is an object of the present invention to provide a filter for processing blood that maintains the fluid channel at the outlet side even under the action of double force by positive pressure at the inlet side and negative pressure at the outlet side during filtration, thus helping to prevent inhibition of blood flow.

The present inventors have conducted much diligent research with the aim of solving the problems mentioned above, and as a result have found that if a portion of the outlet port forming the outlet is purposely situated inside the container body, it is possible to form a gap between the container body and processing blood filter material, and thus to maintain the fluid channel at the outlet side even under the double force of positive pressure at the inlet side and negative pressure at the outlet side during filtration, and to thereby help prevent inhibition of blood flow, and the present invention has been accomplished upon this finding.

Specifically, the invention relates to a filter for processing blood that comprises a flexible container having an inlet and an outlet for blood, and a sheet-like blood processing filter material situated in such a manner so as to partition the inside of the container into an inlet side and an outlet side, wherein the flexible container comprises a container body which houses the blood processing filter material and an outlet port that forms the outlet, and the outlet port has a protrusion that protrudes from the container body into the inside of the container body, the protrusion having a plurality of fluid channel inlets formed at locations that are not in contact with the blood processing filter material.

According to this filter for processing blood, it is possible to maintain the flow of blood even with the action of the double force of positive pressure at the inlet side and negative pressure at the outlet side during filtration, by forming a gap between the blood processing filter material and the container body by a protrusion on the outlet port protruding from the container body. In particular, since a plurality of fluid channel inlets are formed at locations of the protrusion that are not in contact with the blood processing filter material, it is possible to maintain a fluid channel at other fluid channel inlets even when flow at some of the fluid channel inlets has been inhibited, and therefore reduction in the blood treatment rate can be minimized to accomplish stable treatment.

Furthermore, the filter for processing blood may be provided with openings in a gap between the container body and the blood processing filter material formed by the protrusion.

Alternatively, the filter for processing blood may be formed with a protrusion having a contact surface that contacts with the blood processing filter material, and sides formed away from the contact surface at locations not in contact with the blood processing filter material, with a plurality of fluid channel inlets formed on the sides.

Alternatively, the filter for processing blood may be such that the outlet port has an exterior formed on the outside of the container body, and the outlet is formed on the exterior.

Also, the filter for processing blood may have the outlet port connected to a plurality of fluid channel inlets, there being formed a main fluid channel running along the blood processing filter material and branched fluid channels branching from the main fluid channel and communicating with the outlet.

Further, the filter for processing blood may have some of the plurality of fluid channel inlets formed on a side at the inlet side, and the other fluid channel inlets formed on the opposite side of the outlet port.

DESCRIPTION OF THE PREFERRED EMBODIMENTS

Embodiments of the invention will now be explained with reference to the accompanying drawings. The "blood" referred to in the examples includes blood preparations such as whole blood preparations, erythrocyte preparations, platelet preparations and blood plasma preparations for blood transfusion. The outer shape of the filter for processing blood may be in various forms such as a rectangular, disc, elongated disc or ellipsoid shape, but it is preferably a rectangular shape in order to minimize material loss during production, and therefore a rectangular shape will be assumed throughout the embodiments described hereunder.

Figure 1:
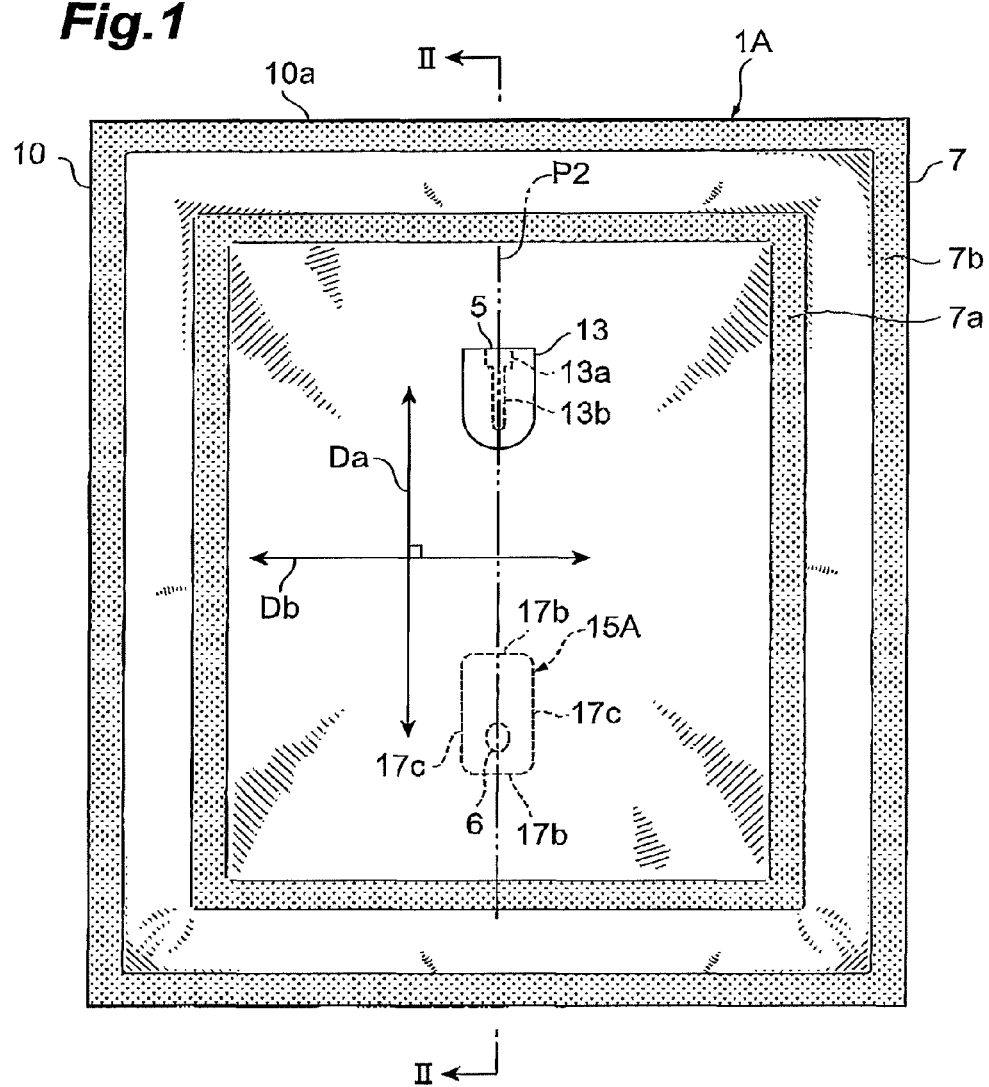
FIG. 1 is a plan view of a filter for processing blood according to a first embodiment of the invention.
Figure 2:
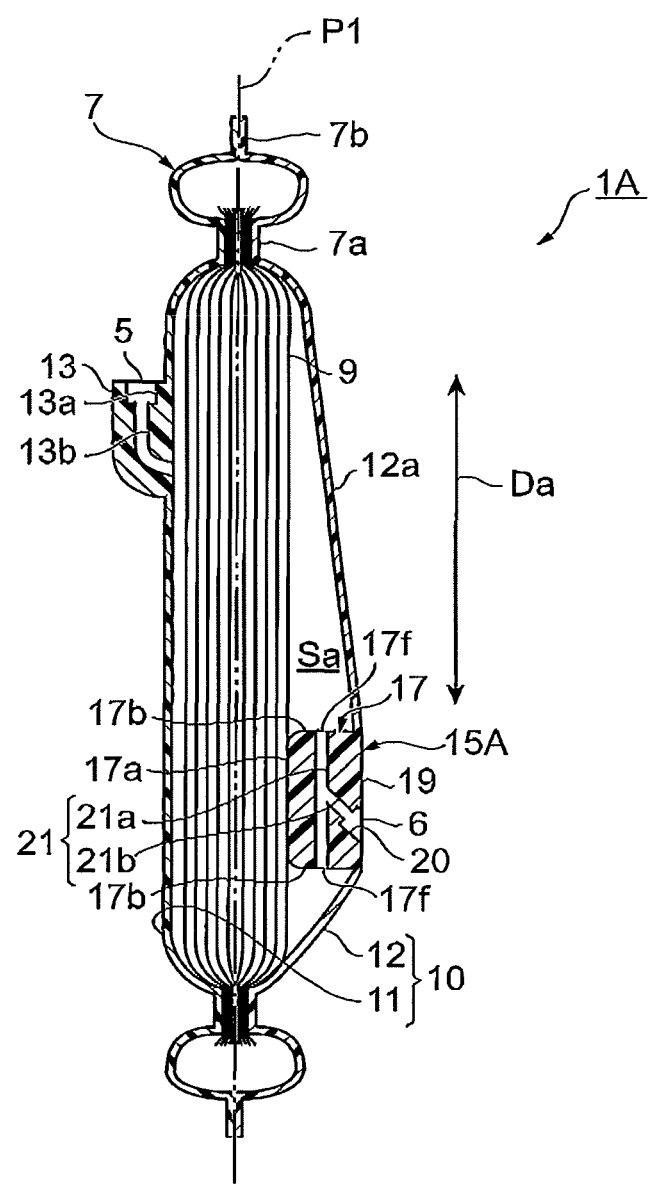
FIG. 2 is a longitudinal section diagram of FIG. 1 along line

First, a filter for processing blood 1A according to a first embodiment will be explained, with reference to FIG. 1 and FIG. 2. The filter for processing blood 1A comprises a flexible container 7 having a blood inlet 5 and outlet 6, and a sheet-like blood processing filter material 9 situated so as to partition the inside of the flexible container 7 into an inlet 5 side and an outlet 6 side. The explanation that follows assumes that the plane along the blood processing filter material 9 is the first plane P1 and a virtual plane containing the center of the inlet 5 and the center of the outlet 6 is the second plane P2, with the direction along the intersection between the first plane P1 and second plane P2 being designated as the longitudinal direction Da, and the direction along the first plane P1, perpendicular to the longitudinal direction Da, being designated as the transverse direction Db.

The flexible container 7 is a rectangular flat container. Here, "flat" is intended to mean a shape with small thickness and wide area. The flexible container 7 comprises a rectangular sheet inlet side container 11 serving as the inlet 5 side, and a rectangular sheet outlet side container 12 serving as the outlet 6 side. The inlet side container 11 and outlet side container 12 are layered via the rectangular blood processing filter material 9, and are bonded so as to fit onto the periphery of the blood processing filter material 9. The belt-like bonding region along the periphery of the blood processing filter material 9 is the inner sealing section 7a, and the inside region further inward than the inner sealing section 7a is the filtering region through which the blood flows.

The inlet side container 11 and outlet side container 12 are also bonded together at their peripheries outside of the inner sealing section 7a. The belt-like bonding region in which the inlet side container 11 and outlet side container 12 are directly bonded constitutes the outer sealing section 7b. The inlet side container 11 and outlet side container 12 form a container body 10 that houses the blood processing filter material 9.

An inlet port 13 forming a blood inlet 5 is integrally formed with the inlet side container 11. The inlet port 13 is situated toward one edge 10a in the longitudinal direction Da of the container body 10. The inlet port 13 is provided protruding outward from the inlet side container 11, and an inlet 5 for supply of blood is formed on the outer surface of the inlet port 13. A connecting hole 13a for a blood tube for blood supply is formed in the inlet 5. An inlet fluid channel 13b is formed in the inlet port 13, connecting the inlet 5 with the inside of the inlet side container 11 (filtering region). The inlet port 13 of this embodiment is formed integrally with the inlet side container 11, but the inlet port 13 and inlet side container 11 may be formed of separate members and integrated by welding or the like.

An outlet port 15A forming a blood outlet 6 is integrally formed in the outlet side container 12. The outlet port 15A is situated in point symmetry with the inlet port 13, relative to the center of the container body 10. The outlet port 15A has a protrusion 17 that protrudes toward the inside of the outlet side container 12. The size of the protrusion 17 of this embodiment in the longitudinal direction Da is a long block shape (roughly cuboid) shape.

The protrusion 17 has a rectangular end face (contact surface) 17a that contacts with the blood processing filter material 9, and sides 17b, 17c that connect the end face 17a with the inner surface of the outlet side container 12. The sides 17b, 17c comprise a pair of short sides 17b formed at both edges in the longitudinal direction Da of the protrusion 17, and a pair of long sides 17c formed at both edges in the transverse direction Db of the protrusion 17. The short sides 17b are smaller relative to the long sides 17c. The end face 17a and the sides 17b, 17c have a bent connection.

A plurality of fluid channel inlets 17f communicating with the filtering region are formed in the protrusion 17. The plurality of fluid channel inlets 17f are provided on each of the pair of short sides 17b at locations not in contact with the blood processing filter material 9. Furthermore, the plurality of the fluid channel inlets 17f have openings in the gap SA formed in between the container body 10 and the blood processing filter material 9 by the protrusion 17. Separately, an outlet 6 through which filtered blood flows is formed in the exterior 19 of the outlet port 15A which is connected flush with the side of the outer surface 12a of the outlet side container 12. An outlet fluid channel 21 is formed in the outlet port 15A, communicating with the outlet 6 of the plurality of fluid channel inlets 17f. A blood tube connecting hole 20 is formed in the outlet 6, for transport of the filtered blood to a bag.

The outlet fluid channel 21 has an aggregating channel (main fluid channel) 21a connecting the pair of fluid channel inlets 17f, and a confluent fluid channel (branched fluid channel) 21b branching from the aggregating channel 21a and connected to the outlet 6. The aggregating channel 21a is a fluid channel lying along the blood processing filter material 9, and the confluent fluid channel 21b is slanted so that when the filter for processing blood 1A is situated vertically with the inlet 5 side up and the outlet 6 side down, a downward incline is formed from the aggregating channel 21a. The outlet fluid channel 21 penetrates the protrusion 17 so as to communicate with the plurality of fluid channel inlets 17f and the outlet 6 within the protrusion 17.

Since the aggregating channel 21a lies along the blood processing filter material 9, the filtered blood that flows along the filter surface is efficiently drawn from the plurality of fluid channel inlets 17f and directed to the confluent fluid channel 21b. Furthermore, since the confluent fluid channel 21b is slanted so as to form a downward incline from the aggregating channel 21a, efficient discharge from the outlet 6 is accomplished. In addition, forming a downward incline reduces circuit bending during blood filtration, allowing more efficient use of the circuit.

The plurality of fluid channel inlets 17f in this embodiment are formed on the pair of short sides 17b of the outlet port 15A. Of the pair of short sides 17b, the short side 17b is the side 17b on the inlet port 13 end (inlet 5 side), and the other short side is the side 17b on the opposite end. The blood supplied from the inlet 5 is filtered by passing through the blood processing filter material 9, and then drawn out through the outlet 6. In this case, since the blood is drawn in not only from the fluid channel inlet 17f at the inlet 5 side but also from the fluid channel inlet 17f at the opposite site of the outlet port 15A, it is possible to reduce pooling of the blood inside the container body 10, and increase blood treatment efficiency.

As mentioned above, the inlet side container 11 and outlet side container 12 form a container body 10 that houses the blood processing filter material 9. The container body 10 is produced using a flexible resin, and for example, it is preferably formed using a synthetic resin sheet member, and even more preferably using a thermoplastic resin. The reason for using a sheet member is that the outer sealing section 7b must have a uniform thickness in the circumferential direction, and the inner sealing section 7a must also have a uniform thickness in the circumferential direction. In other words, so long as the formation is in such a manner that the outer sealing section 7b has a uniform thickness and the inner sealing section 7a has a uniform thickness, it may be formed using a film-like member, or the container body 10 may be constructed from an injection molded article.

The flexible resin used for the inlet side container 11 or outlet side container 12 of this embodiment may be any material that is commercially available as a sheet or film. Examples are suitable materials including thermoplastic elastomers such as soft polyvinyl chloride, polyurethane, ethylene-vinyl acetate copolymer, polyolefins such as polyethylene and polypropylene, hydrogenated styrene-butadiene-styrene copolymer, styrene-isoprene-styrene copolymer or its hydrogenated form, and blends of thermoplastic elastomers with softening agents such as polyolefins and ethylene-ethyl acrylate. Because of potential contact with blood, it is preferred to use soft vinyl chloride, polyurethane, polyolefin, and thermoplastic elastomers comprising them as major components, and more preferably soft vinyl chloride, which are commonly used for medical materials such as blood bags.

The inlet side container 11 may be made entirely of a hard resin, or a portion thereof may be composed of a flexible resin. If at least 10% of the area of the inlet side container 11 is a flexible container, it will be possible to improve the water vapor permeability during autoclave sterilization, and shorten the sterilization time.

The blood processing filter material 9 of this embodiment may be a known filtration medium, for example, a fibrous porous medium, such as a nonwoven fabric or woven fabric, or a porous body having three-dimensional meshed connected pores, such as a sponge structure, whereas materials with poor welding properties such as meshes and screens are not suitable. Examples of materials suitable for use as the blood processing filter material 9 include polypropylene, polyethylene, styrene-isobutylene-styrene copolymer, polyurethanes and polyesters. The blood processing filter material 9 is most preferably a nonwoven fabric, from the viewpoint of productivity.

The sheet-like blood processing filter material 9 may be a single filter element, or it may be formed of a plurality of filter elements. When it is formed of a plurality of filter elements, it preferably comprises a first filter element that removes microaggregates, situated upstream (inlet 5 side), and a second filter element for removal of leukocytes, situated downstream from the first filter element. For example, a filter material composed of a nonwoven fabric with a fiber size of several to several tens of μm may be situated at the inlet 5 side, as the first filter element for removal of aggregates, and then a filter material made of a nonwoven fabric with a fiber size of 0.3-3.0 μm situated as a second filter element for removal of leukocytes, and a post-filter with a specific gap, which is used by layering at the downstream end.

The first and second filter materials may each be composed of a plurality of different filter materials, or only one may be composed of a plurality of filter materials. For example, a first filter material made of a nonwoven fabric having a fiber size of 30-40 μm and/or a nonwoven fabric having a fiber size of 10-20 μm (composed of at least a nonwoven fabric with a fiber size of 30-40 μm and/or a nonwoven fabric with a fiber size of 10-20 μm) may be situated at the upstream end (inlet 5 side), and a second filter material made of a nonwoven fabric having a fiber size of 1.5-2.5 μm and/or a nonwoven fabric having a fiber size of 0.5-1.8 μm (composed of at least a nonwoven fabric with a fiber size of 1.5-2.5 μm and/or a nonwoven fabric with a fiber size of 0.5-1.8 μm) may be situated downstream from the first filter material. A nonwoven fabric with a large fiber size and a nonwoven fabric with a small fiber size may be alternately placed, but preferably the nonwoven fabric with the larger fiber size is situated at the upstream end (inlet 5 side).

Bonding between the inlet side container 11 and outlet side container 12 of the blood processing filter material 9 to form the inner sealing section 7a may be accomplished by high-frequency welding, and the inlet side container 11, outlet side container 12 and blood processing filter material 9 may be welded all together, or the inlet side container 11 and blood processing filter material 9 may be welded, and then the blood processing filter material 9 and outlet side container 12 welded. In fact, so long as the structure is such that the inlet side container 11, blood processing filter material 9 and outlet side container 12 are situated in that order and at least 99% of the blood (blood preparation) entering through the inlet 5 provided at the inlet side container 11 passes through the blood processing filter material 9 and then exits through the outlet 6 provided on the outlet side container 12, without external leakage of blood, the method of bonding the container body 10 and blood processing filter material 9 is not limited to welding and may be another type of method.

With the filter for processing blood 1A according to this embodiment, it is possible to maintain the flow of blood even with the action of the double force of positive pressure at the inlet 5 side and negative pressure at the outlet 6 side during filtration, by forming a gap Sa between the blood processing filter material 9 and the container body 10 by a protrusion 17 on the outlet port 15A protruding from the container body 10. In particular, since a plurality of fluid channel inlets 17f are formed in the protrusion 17 of the outlet port 15A, it is possible to maintain a fluid channel at other fluid channel inlets 17f even when flow at some of the fluid channel inlets 17f has been inhibited, and therefore reduction in the blood treatment rate can be minimized to accomplish stable treatment.

Furthermore, according to the filter for processing blood 1A of this embodiment, the plurality of fluid channel inlets 17f that are formed provide as a result a plurality of non-concentrated liquid flow directions, and therefore the blood processing filter material 9 can be effectively utilized and the treatment rate is increased.

In addition, since the filter for processing blood 1A of this embodiment has the fluid channel inlets 17f formed on the short side 17b (locations not in contact) of the protrusion 17 of the outlet port 15A, it is possible to maintain liquid flow without the fluid channel inlet 17f sticking to the blood processing filter material 9.

A filter for processing blood according to a second embodiment will now be explained, with reference to FIG. 3. Elements and members of the filter for processing blood 1B of this embodiment that correspond to those of the filter for processing blood 1A of the first embodiment will be referred to by like reference numerals, and their explanation will not be repeated. The filter for processing blood 1B of this embodiment and the filters for processing blood 1C-1F of the embodiments described hereunder may be produced using essentially the same materials as the filter for processing blood 1A of the first embodiment.

Figure 3:
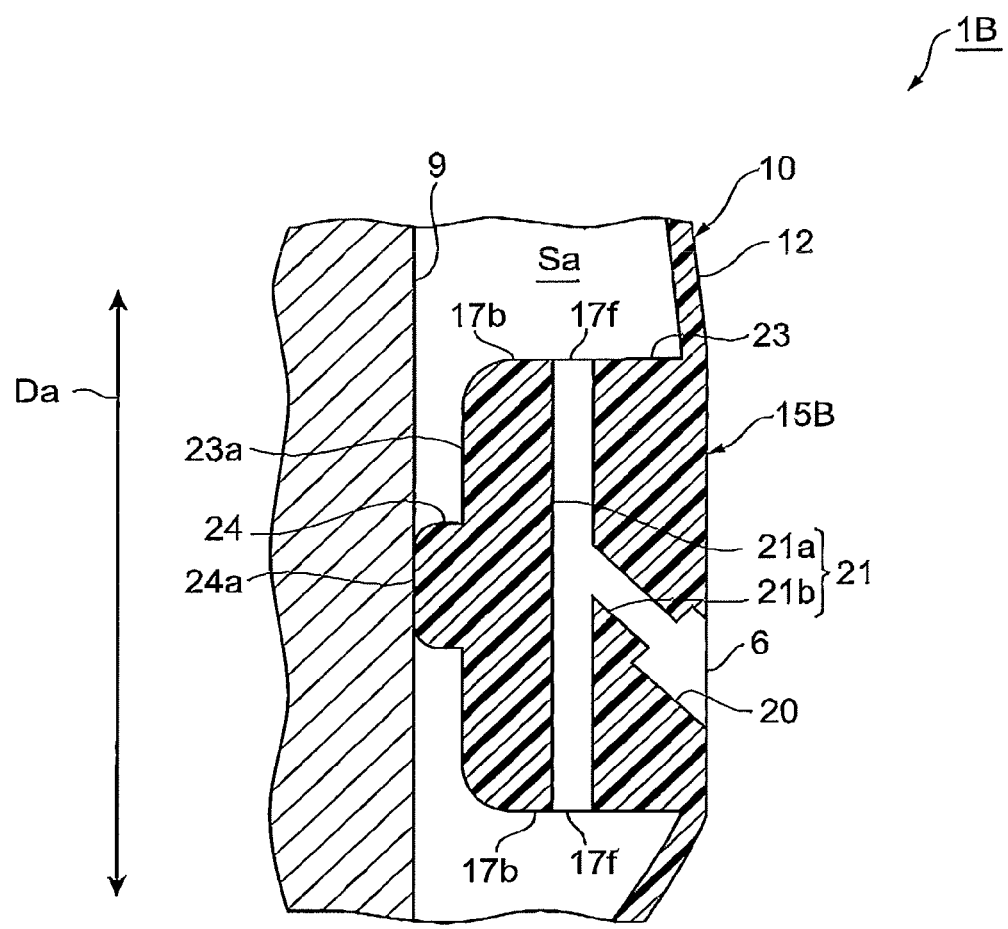
FIG. 3 is a longitudinal section diagram showing a magnified view of the outlet port of a filter for processing blood according to a second embodiment of the invention.

As shown in FIG. 3, the filter for processing blood 1B of the second embodiment differs from the filter for processing blood 1A of the first embodiment in the shape of the protrusion 23 of the outlet port 15B. In the outlet port 1513 of this embodiment, a protrusion 23 is formed in a block shape from the inside of the container body 10 and having a center section 24 protruding from the block-shaped end face 23a. The center section 24 is, for example, cylindrical or rectangular columnar, and the edge face 24a of the center section 24 is the contact surface that contacts with the blood processing filter material 9.

With the filter for processing blood 1B according to this embodiment, it is possible to maintain the flow of blood even with the action of the double force of positive pressure at the inlet 5 side and negative pressure at the outlet 6 side during filtration, by forming a gap Sa between the blood processing filter material 9 and the container body 10 by the protrusion 23 protruding from the container body 10. In particular, since a plurality of fluid channel inlets 17f are formed at locations of the protrusion 23 that are not in contact with the blood processing filter material 9, and the plurality of the fluid channel inlets 17f have openings in the gap SA formed in between the container body 10 and the blood processing filter material 9 by the protrusion 17, it is possible to maintain a fluid channel at other fluid channel inlets 17f even when flow at some of the fluid channel inlets 17f has been inhibited, and therefore reduction in the blood treatment rate can be minimized to accomplish stable treatment.

In addition, the center section 24 of the protrusion 23 in the filter for processing blood 1B of this embodiment is the main section contacting the blood processing filter material 9, and the contact area is extremely narrow. In a mode wherein the center section 24 of the protrusion 23 protrudes to form a contact surface with the blood processing filter material 9, as in this embodiment, the region that is not in contact with the blood processing filter material 9 is widened, and the treatment rate is increased.

A filter for processing blood 1C according to a third embodiment will now be explained, with reference to FIG. 4. Elements and members of the filter for processing blood 1C of this embodiment that correspond to those of the filter for processing blood 1A of the first embodiment will be referred to by like reference numerals, and their explanation will not be repeated.

Figure 4:
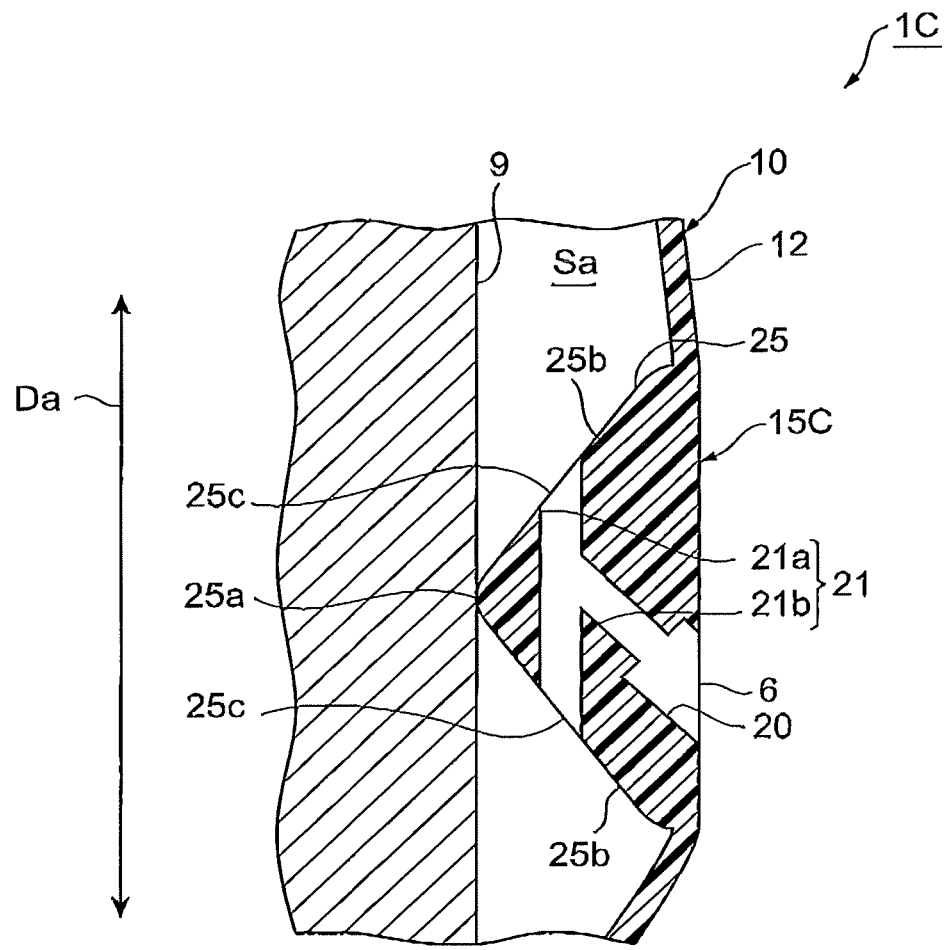
FIG. 4 is a longitudinal section diagram showing a magnified view of the outlet port of a filter for processing blood according to a third embodiment of the invention.

As shown in FIG. 4, the filter for processing blood 1C of the third embodiment differs from the filters for processing blood 1A, 1B of the first and second embodiments in the shape of the protrusion 25 of the outlet port 15C. The outlet port 15C of this embodiment has a protrusion 25 protruding in a shape with a triangular cross-section, from the inside of the container body 10. The tip 25a of the protrusion 25 is a bent surface, and the tip 25a is the contact surface in contact with the blood processing filter material 9. Two fluid channel inlets 25c are formed in the slants 25b of the protrusion 25. The fluid channel inlets 25c and outlet 6 are connected via an outlet fluid channel 21. The protrusion 25 is approximately pyramidal or conical, or it may have a triangular columnar shape in the transverse direction Db.

With the filter for processing blood 1C according to this embodiment, it is possible to maintain the flow of blood even with the action of the double force of positive pressure at the inlet 5 side and negative pressure at the outlet 6 side during filtration, by forming a gap Sa between the blood processing filter material 9 and the container body 10 by a protrusion 25 on the outlet port 15C protruding from the container body 10. In particular, since a plurality of fluid channel inlets 25c are formed at locations of the protrusion 25 that are not in contact with the blood processing filter material 9, and the plurality of the fluid channel inlets 25c have openings in the gap SA formed in between the container body 10 and the blood processing filter material 9 by the protrusion 25, it is possible to maintain a fluid channel at other fluid channel inlets 25c even when flow at some of the fluid channel inlets 25c has been inhibited, and therefore reduction in the blood treatment rate can be minimized to accomplish stable treatment.

In addition, the tip 25a of the protrusion 25 in the filter for processing blood 1C of this embodiment is the main section contacting the blood processing filter material 9, and the contact area can be made extremely narrow. In a mode wherein the tip 25a of the protrusion 25 contacts with the blood processing filter material 9, as in this embodiment, the region that is not in contact with the blood processing filter material 9 is widened, and the treatment rate is increased.

A filter for processing blood 1D according to a fourth embodiment will now be explained with reference to FIG. 5 and FIG. 6. Elements and members of the filter for processing blood 1D of this embodiment that correspond to those of the filter for processing blood 1A of the first embodiment will be referred to by like reference numerals, and their explanation will not be repeated.

Figure 5:
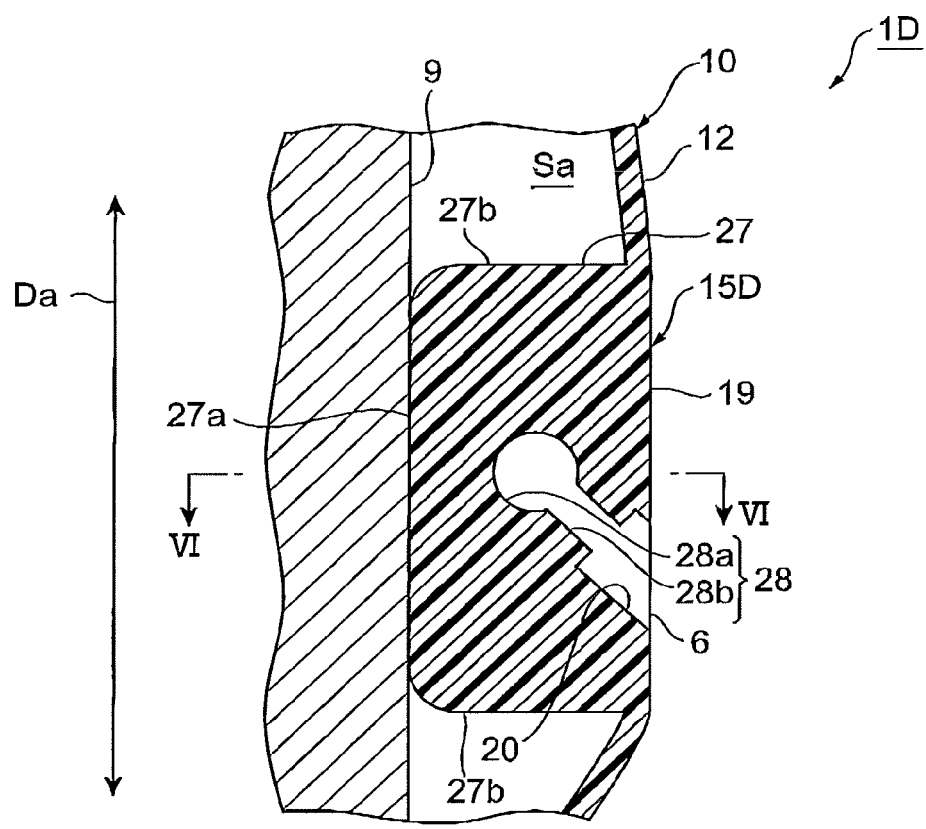
FIG. 5 is a longitudinal section diagram showing a magnified view of the outlet port of a filter for processing blood according to a fourth embodiment of the invention.
Figure 6:
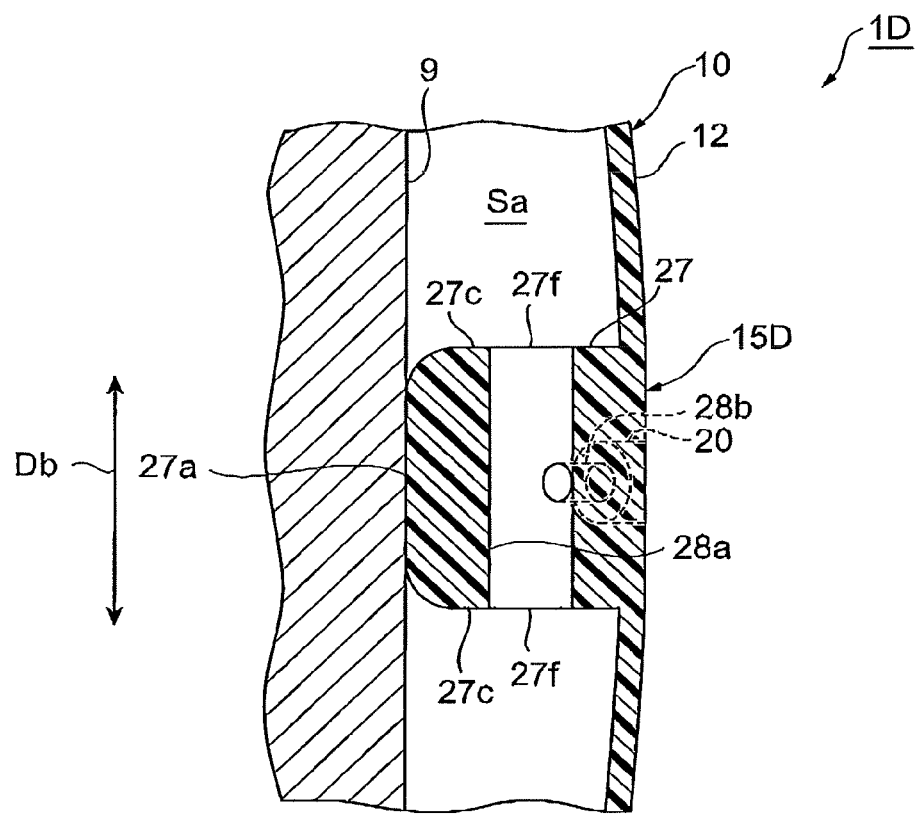
FIG. 6 is a cross-sectional view of FIG. 5 along line VI-VI.

As shown in FIG. 5 and FIG. 6, the protrusion 27 of the outlet port 15D of the fourth embodiment has a long block (cuboid) shape in the longitudinal direction Da, similar to the first embodiment, but the fluid channel inlets 27f and outlet fluid channel 28 formed in the protrusion 27 of the outlet port 15D differ from the outlet port 15A of the first embodiment.

The outlet port 15D and protrusion 27 have an end face (contact surface) 27a in contact with the blood processing filter material 9, and a pair of short sides 27b formed at both ends in the longitudinal direction Da and a pair of long sides 27c formed at both ends in the transverse direction Db, with the fluid channel inlets 27f being formed on the pair of long sides 27c at locations not in contact with the blood processing filter material 9. Furthermore, the plurality of the fluid channel inlets 27f have openings in the gap SA formed in between the container body 10 and the blood processing filter material 9 by the protrusion 27.

The outlet fluid channel 28 is formed in the shape of a T and has an aggregating channel (main fluid channel) 28a connecting the pair of fluid channel inlets 27f, and a confluent fluid channel (branched fluid channel) 28b branching from the aggregating channel 28a and communicating with the outlet 6. The confluent fluid channel 28b is slanted so that when the filter for processing blood 1D is situated vertically with the inlet 5 side up and the outlet 6 side down, a downward incline is formed from the aggregating channel 28a. The outlet 6 is formed on the exterior 19 of the outlet port 150, and a connecting hole 20 is formed in the blood tube at the outlet 6.

With the filter for processing blood 1D according to this embodiment, it is possible to maintain the flow of blood even with the action of the double force of positive pressure at the inlet 5 side and negative pressure at the outlet 6 side during filtration, by forming a gap Sa between the blood processing filter material 9 and the container body 10 by a protrusion 27 on the outlet port 15D protruding from the container body 10. In particular, since a plurality of fluid channel inlets 27f are formed at locations of the protrusion 27 that are not in contact with the blood processing filter material 9, and the plurality of the fluid channel inlets 27f have openings in the gap SA formed in between the container body 10 and the blood processing filter material 9 by the protrusion 27, it is possible to maintain a fluid channel at other fluid channel inlets 27f even when flow at some of the fluid channel inlets 27f has been inhibited, and therefore reduction in the blood treatment rate can be minimized to accomplish stable treatment.

Since the aggregating channel 28a is formed along the transverse direction Db, blood is easily drawn up in an equal manner from the pair of fluid channel inlets 27f and directed to the confluent fluid channel 28b, when the filter for processing blood 1D is oriented vertically. In addition, since the confluent fluid channel 28b forms a downward incline from the aggregating channel 28a, blood collected at the aggregating channel 28a is efficiently discharged from the outlet 6. In addition, forming a downward incline reduces circuit bending during blood filtration, allowing more efficient use of the circuit.

A filter for processing blood 1E according to a fifth embodiment will now be explained, with reference to FIG. 7 and FIG. 8. Elements and members of the filter for processing blood 1E of this embodiment that correspond to those of the filter for processing blood 1A of the first embodiment will be referred to by like reference numerals, and their explanation will not be repeated.

Figure 7:
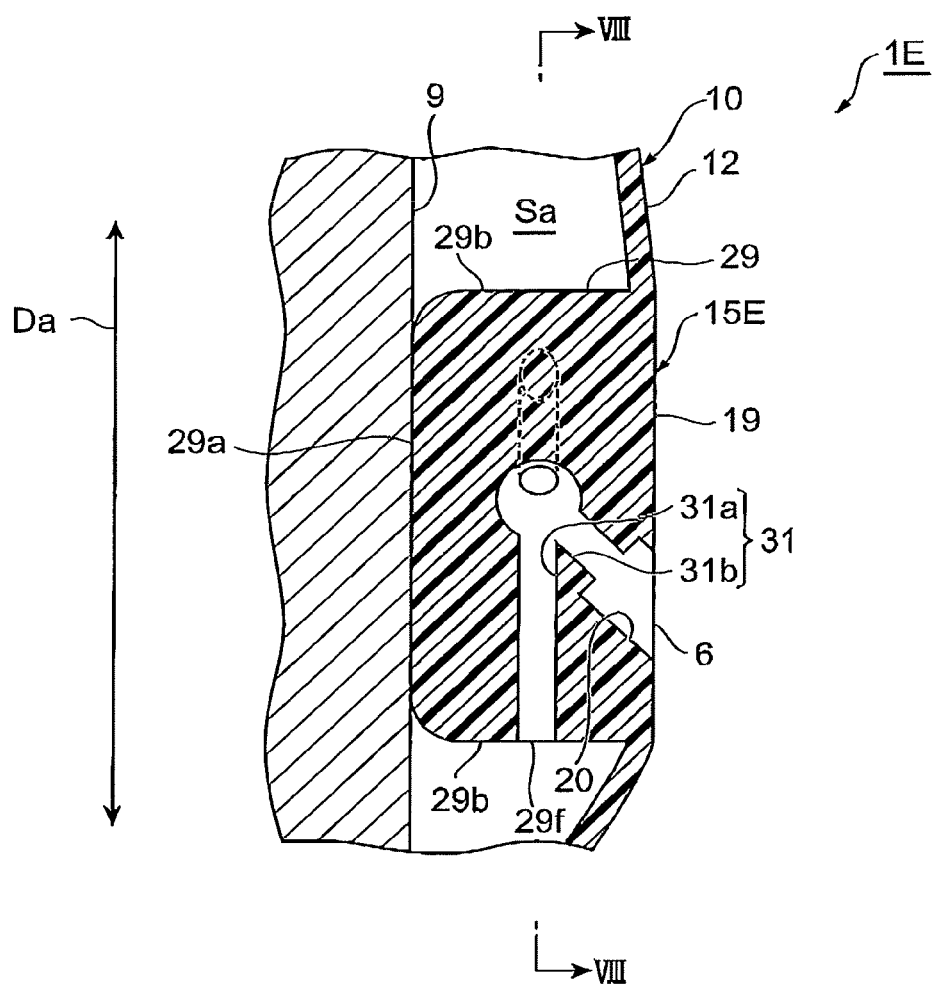
FIG. 7 is a longitudinal section diagram showing a magnified view of the outlet port of a filter for processing blood according to a fifth embodiment of the invention.
Figure 8:
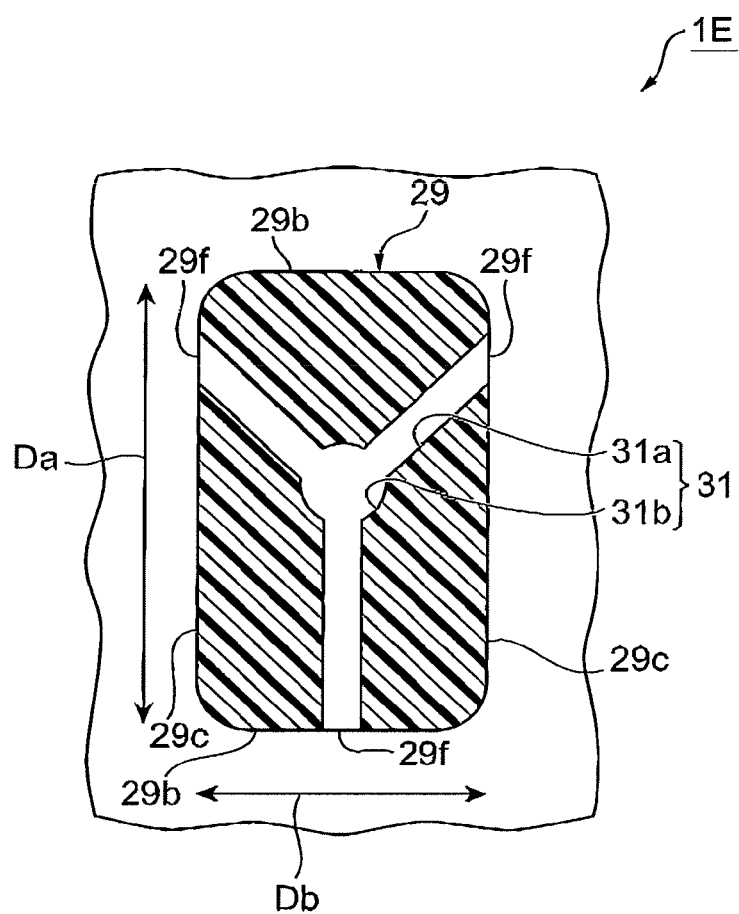
FIG. 8 is a cross-sectional view of FIG. 7 along line VIII-VIII.

As shown in FIG. 7 and FIG. 8, the outlet port 15E of the filter for processing blood 1E of the fifth embodiment has a long block (cuboid) shape in the longitudinal direction Da, similar to the first embodiment, but the fluid channel inlets 29f and outlet fluid channel 31 formed in the protrusion 29 of the outlet port 15E differ from the outlet port 15D of the first embodiment.

The outlet port 15E and protrusion 29 have an end face (contact surface) 29a in contact with the blood processing filter material 9, and a pair of short sides 29b formed at both ends in the longitudinal direction Da and a pair of long sides 29c formed at both ends in the transverse direction Db, with the fluid channel inlets 29f being formed on the pair of long sides 29c and the lower short side 29b. The outlet fluid channel 31 has an aggregating channel (main fluid channel) 31a connecting the three fluid channel inlets 29f, and a confluent fluid channel (branched fluid channel) 31b branching from the aggregating channel 31a and communicating with the outlet 6.

The aggregating channel 31a has a Y-shape (see FIG. 8), and the center of the aggregating channel 31a is connected to the confluent fluid channel 31b. The confluent fluid channel 31b is slanted so that when the filter for processing blood 1E is situated vertically with the inlet 5 side up and the outlet 6 side down, a downward incline is formed from the aggregating channel 31a. The outlet 6 is formed on the exterior 19 of the outlet port 15E, and a connecting hole 20 is formed in the blood tube at the outlet 6.

According to the filter for processing blood 1E of this embodiment, it is possible to maintain the flow of blood even with the action of the double force of positive pressure at the inlet 5 side and negative pressure at the outlet 6 side during filtration, by forming a gap Sa between the blood processing filter material 9 and the container body 10 by the protrusion 29 on the outlet port 15E protruding from the container body 10. In particular, since a plurality of fluid channel inlets 29f are formed at locations of the protrusion 29 that are not in contact with the blood processing filter material 9, it is possible to maintain a fluid channel at other fluid channel inlets 29f even when flow at some of the fluid channel inlets 29f has been inhibited, and therefore reduction in the blood treatment rate can be minimized to accomplish stable treatment.

A filter for processing blood 1F according to a sixth embodiment will now be explained, with reference to FIG. 9. Elements and members of the filter for processing blood 1F of this embodiment that correspond to those of the filter for processing blood 1A of the first embodiment will be referred to by like reference numerals, and their explanation will not be repeated.

Figure 9:
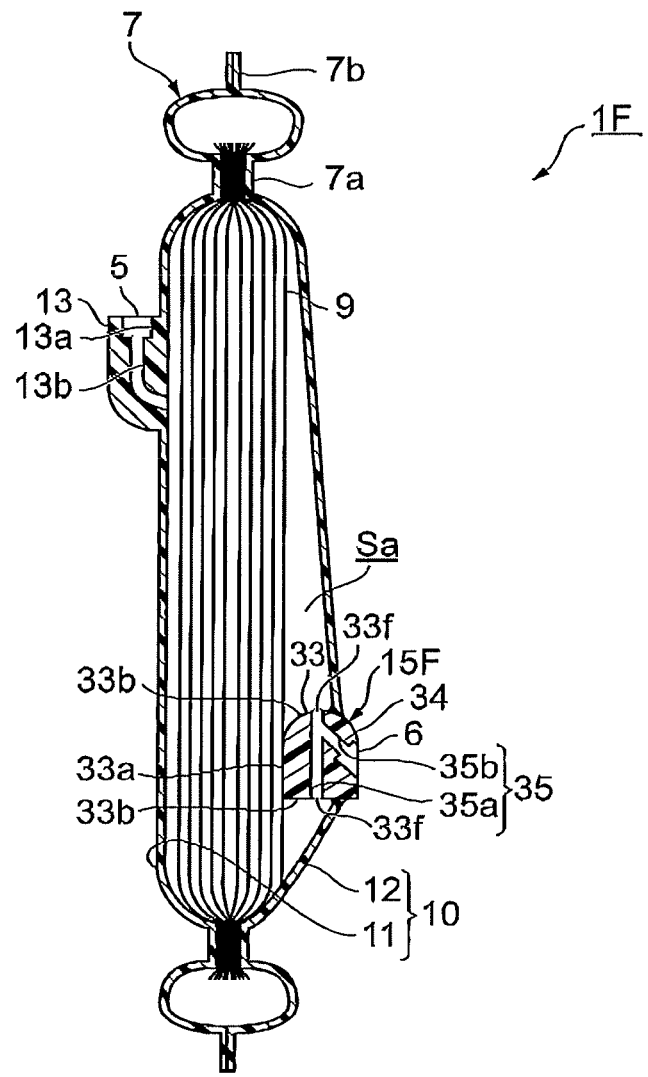
FIG. 9 is a longitudinal section diagram of a filter for processing blood according to a sixth embodiment of the invention.

As shown in FIG. 9, the filter for processing blood 1F of the sixth embodiment differs from the filter for processing blood 1A of the first embodiment in the shape of the protrusion 33 of the outlet port 15F. The outlet port 15F and outlet side container 12 of this embodiment are not formed integrally, but rather an outlet port 15F produced separately from the outlet side container 12 is formed by welding at a prescribed position of the outlet side container 12.

The outlet port 15F comprises a member having one cylindrical end face forming a convex curved surface. A section of the outlet port 15F is exposed on the outer side of the outlet side container 12, while the rest is situated in a manner protruding into the outlet side container 12. The section of the outlet port 15F that is situated in a manner protruding into the outlet side container 12 is the protrusion 33, and the section exposed on the outer side of the outlet side container 12 is the exterior 34.

A portion 33a of the periphery of the protrusion 33 is the contact surface in contact with the blood processing filter material 9. Both end faces 33b, 33c of the protrusion 33 correspond to sides away from the contact surface, the end face 33b of the convex curved surface being the side on the inlet 5 side while the other flat end face 33c is the side on the opposite end. Fluid channel inlets 33f are formed on both end faces 33b, 33c of the protrusion 33, at locations not in contact with the blood processing filter material 9, and the pair of fluid channel inlets 33f are connected via a linear aggregating channel 35a running along the blood processing filter material 9.

An outlet 6 is formed on the exterior 34 of the outlet port 15F, and a confluent fluid channel 35b branching from the aggregating channel 35a is connected to the outlet 6. An outlet fluid channel 35 is formed by the aggregating channel 35a and confluent fluid channel 35b.

According to the filter for processing blood 1F of this embodiment, it is possible to maintain a gap Sa between the blood processing filter material 9 and container body 10 by the protrusion 33 of the outlet port 15F protruding from the container body 10, even with the action of the double force of positive pressure at the inlet 5 side and negative pressure at the outlet 6 side during filtration, and to prevent inhibition of blood flow by the outlet 6 side. In particular, since a plurality of fluid channel inlets 33f are formed in the protrusion 33 of the outlet port 15F, and the plurality of the fluid channel inlets 33f have openings in the gap SA formed in between the container body 10 and the blood processing filter material 9 by the protrusion 33, it is possible to maintain a fluid channel at other fluid channel inlets 33f even when flow at some of the fluid channel inlets 33f has been inhibited, and therefore reduction in the blood treatment rate can be minimized to accomplish stable treatment.

Since a portion of the outlet port 15F is outside of the outlet side container 12 in the filter for processing blood 1F of this embodiment, it is easy to anchor the position of the filter for processing blood 1F and anchor the outlet port 15F itself, during the filter production steps in an automatic line.

EXAMPLES

The present invention will now be described in greater detail by examples, with the understanding that the invention is not limited to the examples.

A 320 g portion of erythrocyte preparation (storage conditions: 4° C., 2 days) at room temperature was filtered with a filter by gravitational force with a filtering drop of 1 m (the distance from the blood bag containing the preparation to the filter below it). The filter inlet tube length was 42 cm, and the filter outlet tube length was 50 cm. The filtration time was defined as the time from initial flow of the fluid until the blood disappeared from the blood bag, filter inlet tube and filtration side at the filter inlet side. The residual blood amount was the value of the blood treatment volume minus the amount of collected blood. This was carried out for three samples, and the average value was determined.

Example 1

Example 1 is a specific mode of a filter for processing blood according to the first embodiment described above. In Example 1, filtration was conducted with the filter for processing blood situated vertically with the inlet side up and the outlet side down, and with the end face of the protrusion of the outlet port contacting the blood processing filter material. The sides of the protrusion were not in contact with the blood processing filter material, and two fluid channel inlets were formed on the upper and lower short sides. Example 1 has an increased contact area between the outlet port and blood processing filter material. With filtering of a prescribed amount of sample fluid in Example 1, the filtration time was 44.8 minutes and the residual amount in the container body was 38.3 ml.

Example 2

Example 2 is a specific mode of a filter for processing blood according to the second embodiment described above. In Example 2, filtration was conducted with the filter for processing blood situated vertically with the inlet side up and the outlet side down, and with the center section of the end face of the protrusion of the outlet port protruding and as the major section of contact with the blood processing filter material. The end face and sides of the protrusion, other than the center section, were not in contact with the blood processing filter material, and two fluid channel inlets were formed on the upper and lower short sides. Example 2 has a decreased contact area between the outlet port and blood processing filter material. With filtering of a prescribed amount of sample fluid in Example 2, the filtration time was 41.6 minutes and the residual amount in the container body was 38.2 ml.

Example 3

Example 3 is a specific mode of a filter for processing blood according to the third embodiment described above. In Example 3, filtration was conducted with the filter for processing blood situated vertically with the inlet side up and the outlet side down, and with the tip of the protrusion of the outlet port as the major section contacting the filter material. The sides other than the tip were not in contact with the blood processing filter material, and two fluid channel inlets were formed on the sides other than the tip. Example 3 has a decreased contact area between the outlet port and blood processing filter material. With filtering of a prescribed amount of sample fluid in Example 3, the filtration time was 40.3 minutes and the residual amount in the container body was 36.7 ml.

Example 4

Example 4 is a specific mode of a filter for processing blood according to the fourth embodiment described above. In Example 4, filtration was conducted with the filter for processing blood situated vertically with the inlet side up and the outlet side down. The outlet port was a long block shape in the transverse direction, and the end face of the protrusion of the outlet port was in contact with the filter material. The sides of the protrusion were not in contact with the blood processing filter material, and two fluid channel inlets were formed on the pair of sides formed at both ends in the transverse direction. Example 4 has an increased contact area between the outlet port and blood processing filter material. With filtering of a prescribed amount of sample fluid in Example 4, the filtration time was 48.0 minutes and the residual amount in the container body was 39.2 ml.

Example 5

Example 5 is a specific mode of a filter for processing blood according to the fifth embodiment described above. In Example 5, filtration was conducted with the filter for processing blood situated vertically with the inlet side up and the outlet side down, and with the end face of the protrusion of the outlet port contacting the blood processing filter material. The sides of the protrusion were not in contact with the blood processing filter material, and three fluid channel inlets were formed on the sides of the protrusion. Example 5 has an increased contact area between the outlet port and blood processing filter material. With filtering of a prescribed amount of sample fluid in Example 5, the filtration time was 44.2 minutes and the residual amount in the container body was 38.2 ml.

Comparative Example 1

Figure 10:
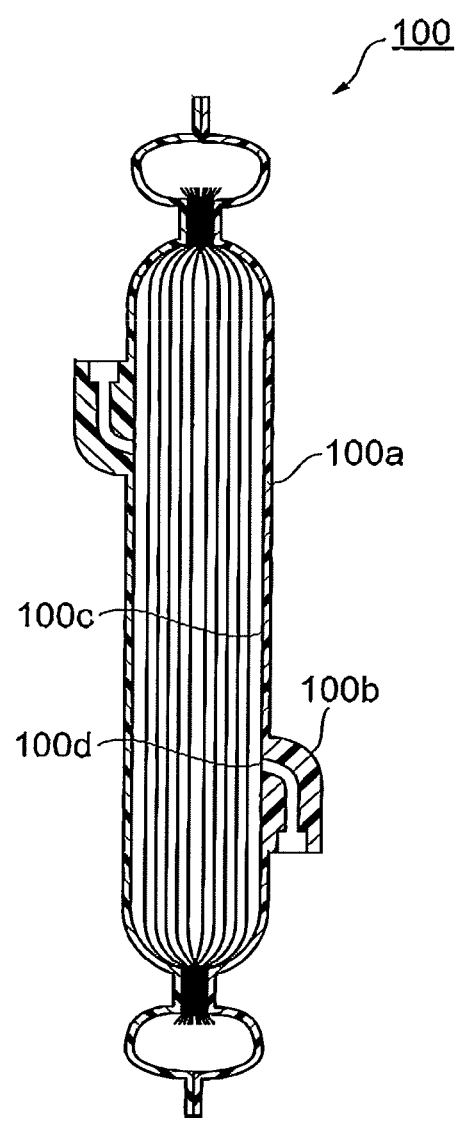
FIG. 10 is a longitudinal section diagram of a filter for processing blood according to Comparative Example 1.

FIG. 10 is a longitudinal section diagram of a filter for processing blood 100 according to Comparative Example 1. In Comparative Example 1, the outlet port 100b is provided in a manner protruding out of the container body 100a. In Comparative Example 1, the entire inner surface area 100c of the container body 100a is the contact surface assumed to be in contact with the blood processing filter material, and a single fluid channel inlet 100d is formed at a location of contact with the blood processing filter material. With filtering of a prescribed amount of sample fluid in Comparative Example 1, the filtration time was 64.0 minutes and the residual amount in the container body was 36.2 ml.

Comparative Example 2

Figure 11:
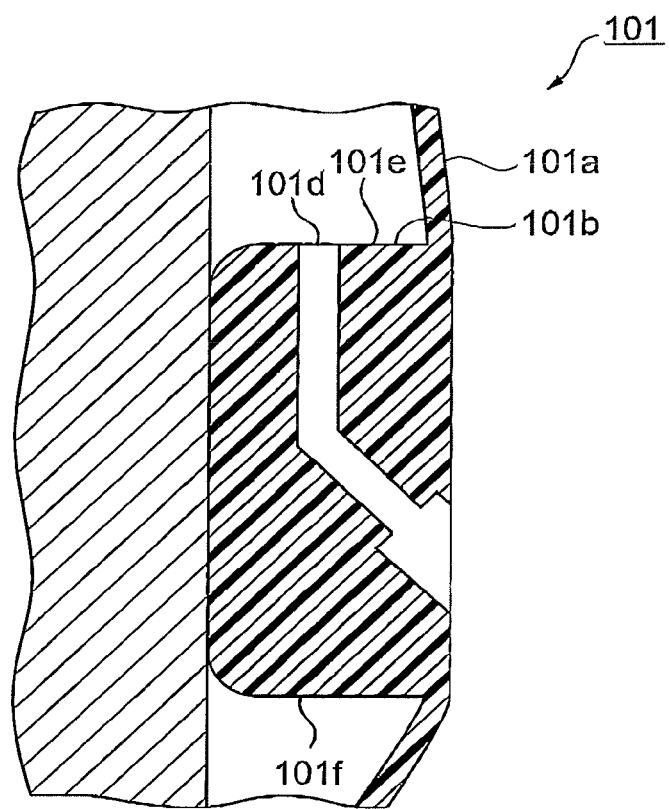
FIG. 11 is a longitudinal section diagram showing a magnified view of the outlet port of a filter for processing blood according to Comparative Example 2.

FIG. 11 is a longitudinal section diagram showing a magnified view of the outlet port 101a of a filter for processing blood 101 according to Comparative Example 2. The outlet port 101b of Comparative Example 2 has a block-shaped protrusion provided in a manner protruding inward from the container body 101b. Only a single fluid channel inlet 101d is formed in Comparative Example 2. The fluid channel inlet 101d is formed only on the upper short side 101e, while the fluid channel inlet 101d is not formed on the lower short side 101f. With filtering of a prescribed amount of sample fluid in Comparative Example 2, the filtration time was 51.2 minutes and the residual amount in the container body was 39.3 ml.

Comparative Example 3

Figure 12:
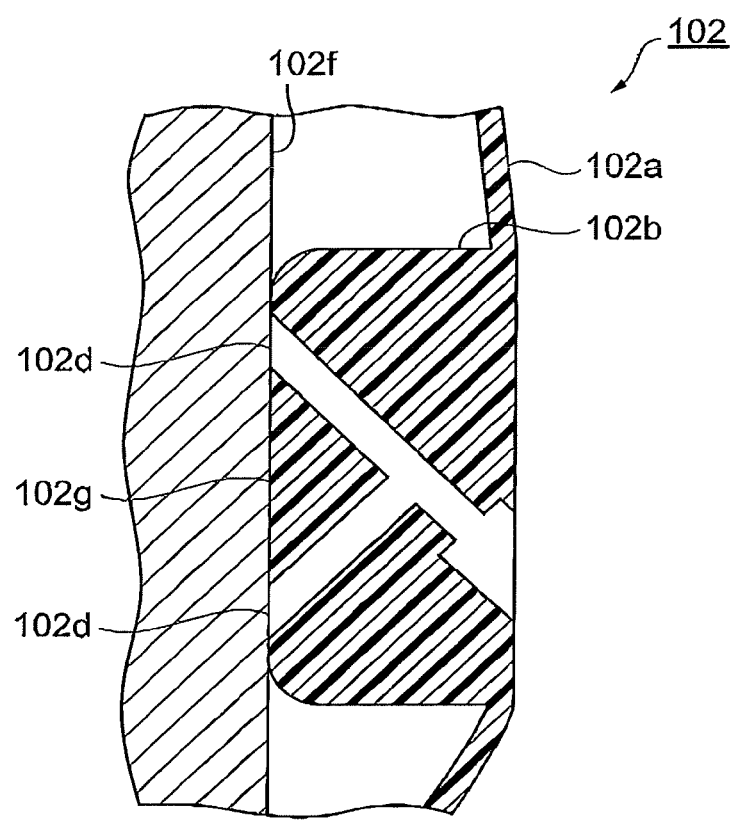
FIG. 12 is a longitudinal section diagram showing a magnified view of the outlet port of a filter for processing blood according to Comparative Example 3.

FIG. 12 is a longitudinal section diagram showing a magnified view of the outlet port 102b of a filter for processing blood 102 according to Comparative Example 3 The outlet port 102b of Comparative Example 3 has a block-shaped protrusion provided in a manner protruding inward from the container body 102a. Two fluid channel inlets 102d are formed in the protrusion, and the two fluid channel inlets 102d are formed on the end face 102g in contact with the blood processing filter material 102f. With filtering of a prescribed amount of sample fluid in Comparative Example 3, the filtration time was 57.6 minutes and the residual amount in the container body was 41.2 ml.

[Overall Evaluation]

With the filters for processing blood of Examples 1-5, the filtration time was much shorter than with the filters for processing blood of Comparative Examples 1-3. More specifically, the results demonstrated that reducing the contact area between the outlet port and blood processing filter material shortens the filtration time. Moreover, the results showed that residual blood is reduced at the outlet side if the fluid channel inlet is below the filter for processing blood in the longitudinal direction.

What is claimed is:

1. A filter for processing blood that comprises:
a flexible container having an inlet and an outlet for blood, and a sheet-like blood processing filter material situated in such a manner so as to partition the inside of the container into an inlet side and an outlet side, and an outlet fluid channel that penetrates a protrusion so as to communicate with a plurality of fluid channel inlets and the outlet within the protrusion,
wherein the flexible container comprises a container body which houses the blood processing filter material and an outlet port having the outlet, and
the outlet port has the protrusion that protrudes from the container body into the inside of the container body, the protrusion having a plurality of fluid channel inlets formed at locations that are not in contact with the blood processing filter material.

2. The filter for processing blood according to claim 1, wherein the plurality of fluid channel inlets have an opening in a gap between the container body and the blood processing filter material formed by the protrusion.

3. The filter for processing blood according to claim 1, wherein the protrusion has a contact surface that contacts with the blood processing filter material, and side walls formed away from the contact surface at locations not in contact with the blood processing filter material, with at least some of the plurality of fluid channel inlets are formed on the side walls.

4. The filter for processing blood according to claim 3, wherein the outlet port has an exterior formed on the outside of the container body, and the outlet is formed on the exterior.

5. The filter for processing blood according to claim 4, the plurality of fluid channel inlets being connected to the outlet port and an outlet fluid channel being formed having a main fluid channel running along the blood processing filter material and branched fluid channels branching from the main fluid channel and communicating with the outlet.

6. The filter for processing blood according to claim 5, further comprising at least some of the plurality of fluid channel inlets being formed on the side at the inlet side and at least some of the plurality of fluid channel inlets being formed on the opposite side of the outlet port.

7. A filter for processing blood that comprises a flexible container having an inlet and an outlet for blood, and a sheet-like blood processing filter material situated in such a manner so as to partition the inside of the container into an inlet side and an outlet side,
wherein the flexible container comprises a container body which houses the blood processing filter material and an outlet port having the outlet, and
the outlet port has a protrusion that protrudes from the container body into the inside of the container body, the protrusion having a plurality of fluid channel inlets formed at locations that are not in contact with the blood processing filter material, and a gap formed by the protrusion between the container body and the blood processing filter material is wider on a side closer to the protrusion than on a side farther from the protrusion such that the gap narrows in a direction extending from the protrusion towards ends of the filter.

8. The filter for processing blood according to claim 7, wherein the protrusion has a contact surface that contacts with the blood processing filter material, and side walls formed away from the contact surface at locations not in contact with the blood processing filter material, with at least some of the plurality of fluid channel inlets are formed on the side walls.

9. The filter for processing blood according to claim 7, the plurality of fluid channel inlets being connected to the outlet port and an outlet fluid channel being formed having a main fluid channel running along the blood processing filter material and branched fluid channels branching from the main fluid channel and communicating with the outlet.

10. The filter for processing blood according to claim 7, further comprising at least some of the plurality of fluid channel inlets being formed on the side at the inlet side and at least some of the plurality of fluid channel inlets being formed on the opposite side of the outlet port.

11. The filter for processing blood according to claim 7, wherein the outlet port has an exterior formed on the outside of the container body, and the outlet is formed on the exterior.

\* \* \* \* \*